United States Patent
Walte et al.

(10) Patent No.: US 6,636,811 B1
(45) Date of Patent: Oct. 21, 2003

(54) METHOD AND DEVICE FOR IDENTIFYING GASEOUS COMPOUNDS

(75) Inventors: Andreas Walte, Schwerin (DE); Wolf Munchmeyer, Schwerin (DE); Gerhard Matz, Buchholz (DE); Torsten Hunte, Hamburg (DE); Stefan Dohren, Tangstedt (DE)

(73) Assignee: WMA Airsense Analysentechnik GmbH, Schwerin (DE)

( * ) Notice: Subject to any disclaimer, the term of this patent is extended or adjusted under 35 U.S.C. 154(b) by 0 days.

(21) Appl. No.: 09/623,118
(22) PCT Filed: Feb. 19, 1999
(86) PCT No.: PCT/DE99/00457
§ 371 (c)(1), (2), (4) Date: Oct. 24, 2000
(87) PCT Pub. No.: WO99/42820
PCT Pub. Date: Aug. 26, 1999

(30) Foreign Application Priority Data

Feb. 24, 1998 (DE) .......................................... 198 07 658

(51) Int. Cl.[7] ............................................. G01N 31/00
(52) U.S. Cl. ............................ 702/24; 702/22; 702/23; 702/25; 702/30
(58) Field of Search ............................... 702/22, 23–25, 702/30, 100, 116, 120, 126; 422/63, 69; 435/320; 204/603

(56) References Cited

U.S. PATENT DOCUMENTS

| | | | |
|---|---|---|---|
| 4,895,017 A | 1/1990 | Pyke et al. | 73/23 |
| 5,469,369 A | 11/1995 | Rose-Pehrsson et al. | 364/497 |
| 5,494,826 A | 2/1996 | Stetter et al. | 436/147 |
| 5,668,735 A * | 9/1997 | Dominguez et al. | 364/497 |
| 5,866,907 A * | 2/1999 | Drukier et al. | 250/366 |
| 6,122,042 A * | 9/2000 | Wunderman et al. | 356/73 |

FOREIGN PATENT DOCUMENTS

EP 0670490 9/1995

OTHER PUBLICATIONS

T Nakamoto et al., Active/odor sensing system using automatically controlled gas blender and numerical optimization technique Jun. 1994, Sensors and Actuators. B Chemical B20 (1994) Jun., Nos.2/3, Lausanne, CH, pp. 131–137.*

Nakamoto T et al.: "Active gas/odor sensing system using automatically controlled gas blender and numerical optimization technique".

Sensors and Actuators B, vol. B20, No. 2/03, Jun. 1, 1994 pp. 131–137.

X000478152 ISSN: 0925–4005 p. 132–p. 134; figures 1,2,4
JP 05 273170 A (Tokyo Instute of Technology).

* cited by examiner

Primary Examiner—Marc S. Hoff
Assistant Examiner—Felix Suarez
(74) Attorney, Agent, or Firm—Horst Kasper

(57) ABSTRACT

The invention relates to a device for identifying gaseous compounds, comprising a sensor array (1) having, for instance, ten gas sensors (2) in the form of semiconductor gas sensors. Said sensor array (1) has a supply line (3) with an inlet (4) and an outlet (5). A switchable three-way valve (6) is located in the supply line (3), to which a selective collector unit (7) is attached. Said collector unit (7) comprises a special adsorber (8), a heater (9) and a separate feed pump (10) with a flow sensor (11). A secondary line (12), in which a dilution unit (13) is arranged, discharges into the feed line (3) between the three-way valve (6) and the sensor array (1). A feeding and control unit (16) also having a feed pump (17) with a flow sensor (18) is located in the area of the outlet (5) of the sensor array (1). An electrical line (19) leading to an evaluation computer (20) branches off from the sensor array (1).

33 Claims, 1 Drawing Sheet

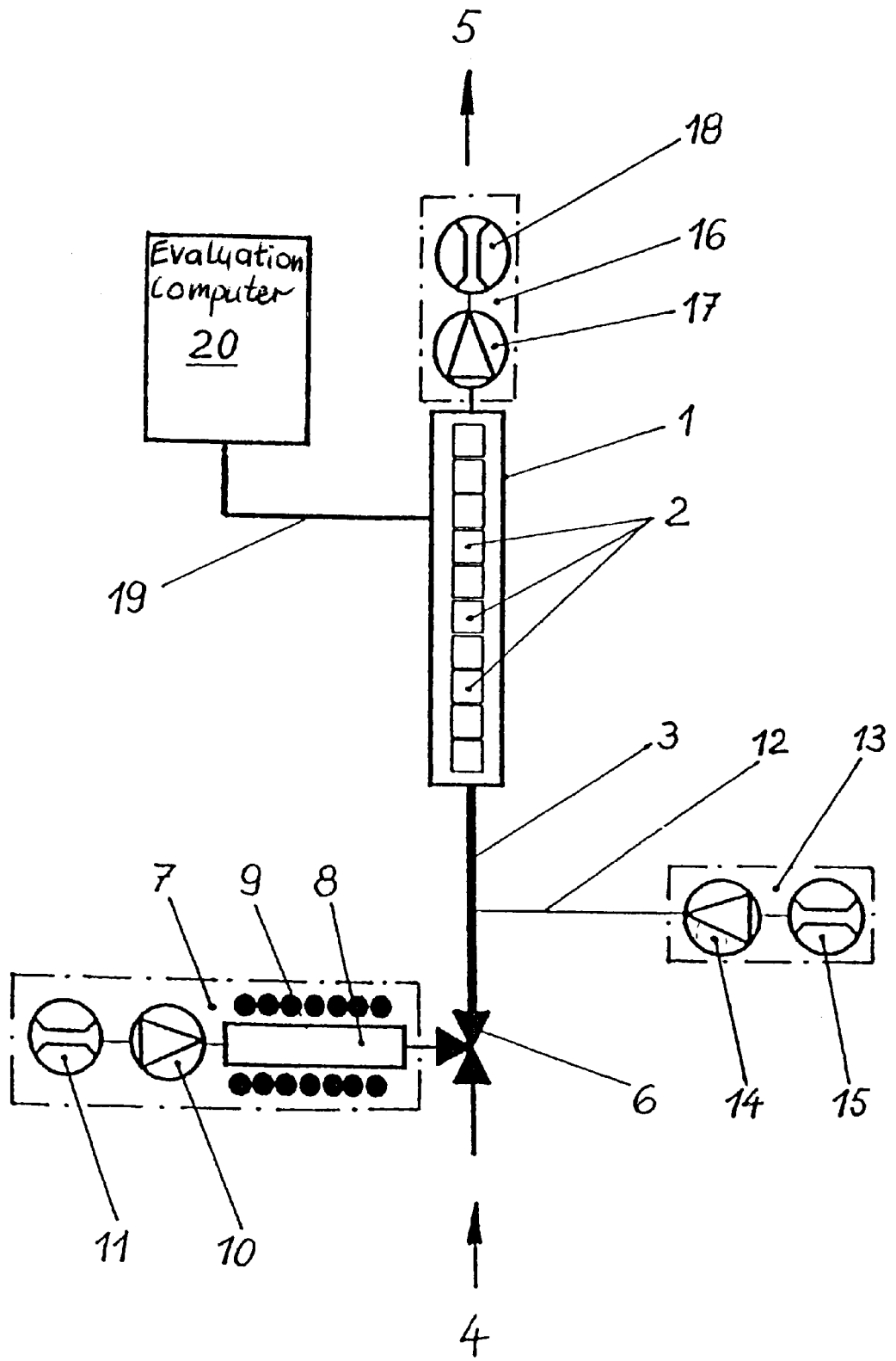

METHOD AND DEVICE FOR IDENTIFYING GASEOUS COMPOUNDS

The Invention relates to a method for determining gasous compounds, wherein a sample gas stream is lead to a sensory array with several gas sensors (2), wherein the electrical output signals of the individual gas sensors (2) are captured by the evaluation computer.

Such methods and apparatuses are employed for the identification of gas mixtures, in particular in the food processing industry.

By now it has become of large importance to investigate and monitor, for example, food products with respect to quality or the environment with respect to a loading of the environment. For this purpose gas mixture samples are taken from the products with desired quality features and characteristic images are generated with the aid of suitable sensors. These images are stored and serve as comparison patterns for all successive investigations.

Such methods are known for a longer time. Apparatuses and arrangements operating according to this method have been employed more heavily in recent times as 'electronic nose'. These apparatuses comprise a unit for taking gas samples with a pump and a gas flow sensor, a sensor array with several, for example, 10 different gas sensors, and an evaluation computer. For example, semiconductor gas sensors are unspecific sensors such that in the presence of gas mixtures all sensors react, however, each sensor delivers a different signal. All these different signals result in an overall picture diagram. The shape of this image characterizes the gas mixture and forms the basis as a pattern for the further investigations. It is also known to employ a spectrometer instead of a sensor array with several gas sensors, for example, an ion mobility spectrometer or an optical spectroscope or a combination of the recited apparatuses.

However, it has been shown that such method is unsuitable for such gas mixtures, where in addition to the compounds of interest there are present also other compounds in much larger concentrations. These are in general easily volatile compounds such as for example ethanol in alcoholic beverages. Because of the high concentration of the ethanol the sensors react mainly relative to the ethanol and not to aroma materials and the sensors thereby falsify the measurement results. A further disadvantage of this method comprises that many gas sensors do not generate linear concentration characterizing curves with the same materials and different concentrations. This leads to different patterns and thus to an increased expenditure for rerecognition of a gas mixture. It is also disadvantageous that the sensors change in the course of time and that for this reason, the patterns have to the renewed again and again.

There exists therefore the purpose to develop a method and an apparatus of the recited kind, which linearizes the characterizing curves of the individual sensors.

A further object comprises to create the possibility to further free, as required, the gas samples in addition from easily volatile gas components.

This object is accomplished the method for determining gaseous compounds, wherein a sample gas stream is thinned with a stream of air prior to the feeding into the sensor array and wherein thereby the concentration of the sample gas stream is kept constant to a predetermined value. The electrical output signal gas sensor array are captured by the evaluation computer and converted into a characterizing diagram, are stored and are compared with the diagrams of other gas mixtures. The apparatus for determining of gaseous compound, comprising also a transfer and control unit (16) for the controlled transport of a sample gas stream through the sensor array (1), a switchable three way valve (6) is disposed in a feed line (3) with an inlet port (4). The switchable three way valve (6) is in connection with a selective collection unit (7) and wherein a sideline (12) with a thinning unit (13) joins between the three-way valve (6) and the sensor array (1).

The recited disadvantages of the state-of-the-art are eliminated with the present invention. Thus, gaseous compounds can now be recognized with high precision and independent of their concentration. This improves the quality of the comparison measurements substantially. The gas sensors are thereby treated with care such that they are loaded only with a concentration degree far below the saturation limit.

The method is also advantageous with respect to that also gaseous compounds with non-selectionable components can be subjected to such a comparative investigation by a preceding treatment of the gas sample stream in a selective collection unit. This extends the field of application substantially for the method.

The apparatus according to the present invention is constructed based on the switchable three way valve of the apparatus dispsoed in the feed line to the sensor array such that the sample gas stream can be lead as desired over the selective collection unit or passed by the selective collection unit. This selective collection unit is equipped in a special way with a reversible feed transport pump, wherein the reversible feed transport pump fills the selective collection unit by its suction power and empties then again the selective collection unit based on its pressure power. This simplifies the device-technical construction of the apparatus.

It is also advantageous to employ generally known absorbents for the enrichment of the selectionable gas components.

The invention is to be illustrated in more detail by way of a schematic illustration.

The device for the performing of the method for determining the gaseous component comprises mainly a sensor array 1 with for example ten gas sensors 2 formed as semiconductor gas sensors. This sensor array 1 comprises on the one hand a feed line 3 with an inlet port 4 and on the other hand a discharge port 5. A switchable three way valve 6 is disposed in the feed line 3, and a selective collection unit 7 is connected to the switchable three way valve 6. This collection unit 7 comprises a special adsorbent 8 and a heater 9 as well as a separate feed transport pump 10 with the a flow sensor 11 for the feed transport pump 10. A sideline 12 connects to the feed line 3 between the three way valve 6 and the sensor array 1, wherein a thinning unit 13 is disposed in the sideline 12. This thinning unit 13 is also furnished with a feed transport pump 14 and a flow sensor 15 for the feed transport pump 14 as well as with an air filter not illustrated. A transport and control unit 16 is disposed in the region of the discharge port 5 of the sensor array 1, wherein the transport and control unit 16 again comprises a feed transport pump 17 and a flow sensor 18 for the feed transport pump 17. An electric conduit branches off from the sensor array 1 and leads to an evaluation computer 20, wherein the evaluation computer 20 is furnished with contact to all flow sensors 11, 15 and 18 through connection lines not illustrated.

A sample is taken off a gas mixture for determining the gas mixture, wherein the feed transport pump 17 of the transport and control unit 16 sucks in a predetermined flow of the gas mixture through the inlet port 4 and transports the predetermined flow of the gas mixture through the sensor array 1. At the same time the feed transport pump 14 of the thinning unit 13 feeds a predetermined flow of filtered fresh air to the sample gas stream in the feed line 3. The mixing ratio of the sample gas stream and of the air stream is selected such that the work point of the gas sensor 2 is fixed in the lower region of its nonlinear concentration curve. The most sensitive or the quickest gas sensor reacts thereby preferably always at a certain work point such that always the same images of different measurements of a same sample gas stream result independently of the concentration of the gas mixture. As required and in the following, the concentration of the gas mixture can be calculated through the mixing ratio displayed at the evaluation computer 20 and therefore known.

The mixing process is continuously monitored and regulated by the evaluation computer 20. The electric signals of all gas sensors 2 are captured at the evaluation computer 20, are optically imaged with a diagram and stored. This diagram characterizing for the measured sample gas stream is then available for later identification of other gas mixtures as a sample pattern.

If a gas mixture is present with a part of easily volatile components, wherein the easily volatile components are not selectionable based on their approximately same concentration, and wherein the easy volatile components, because of their high concentration, mainly act on the gas sensors 2, then the selective collection unit 7 is employed. The feed transport pump 10 of the selective collection unit 7 sucks the sample gas stream into the adsorber 8, wherein the feed transport pump 10 is automatically controlled by the evaluation computer 20 and by the flow sensor 11. The required medium volatile and hardly volatile aroma materials of the gas mixture are here enriched on special adsorbents, while the easily volatile gas components break through and thus are not enriched. A following thermal desorption, introduced by the heater 9, dissolves the medium volatile aroma materials from the absorbents. These aroma materials are lead back again into the feed line 3 based on a computer controlled reversal of the transport direction of the feed transport pump 10 and these aroma materials are transported in and through the sensor array 1 in cooperation with the feed transport pump 17 of the transport and control unit 16. At the same time again filtered fresh air is mixed in through the thinning unit 13 in the manner already described.

LIST OF REFERENCE NUMERALS

1 sensor array
2 gas sensor
3 feed line
4 inlet port
5 outlet port
6 switchable three way valve
7 selective collection unit
8 adsorber
9 heater
10 feed transport pump
11 flow sensor
12 sideline
13 thinning unit
14 feed transport pump
15 flow sensor
16 transport and control unit
17 feed transport pump
18 flow sensor
19 electric conduit
20 evaluation computer

What is claimed is:

1. Method for determining gaseous compounds, wherein a sample gas stream is lead to a sensor array (1) with several gas sensors (2), wherein the electrical output signal of the individual gas sensors (2) are captured by the evaluation computer (20), wherein the electrical output signals are converted into a characterizing image, are stored and are compared with the images of other gas mixtures,
   characterized in that the sample gas stream is thinned with a stream of air prior to the feeding into the sensor array (1) and wherein thereby the concentration of the sample gas stream is kept constant to a predetermined value below the saturation concentration.

2. Method for determining gaseous compounds,
   wherein a sample gas stream is lead to a sensor array (1) with several gas sensors (2), wherein the electrical output signal of the individual gas sensors (2) are captured by the evaluation computer (20), wherein the electrical output signals are converted into a characterizing image, are stored and are compared with the characterizing images of other gas mixtures,
   characterized in that the sample gas stream is thinned with a stream of air prior to the feeding into the sensor array (1) and wherein thereby the concentration of the sample gas stream kept constant to a predetermined value below the saturation concentration,
   wherein the sample gas stream contains easily volatile gas components and wherein the sample gas stream is separated and is freed of easily volatile gas components prior to the feeding into the sensor array (1) and prior to the mixing with the air stream.

3. Method according to claim 2, wherein the sample gas stream contains easily volatile gas components, medium volatile gas components and hardly volatile components and wherein the medium and hardly volatile gas components of the sample gas stream are separated from the easily volatile gas components of the sample gas stream by adsorption and in the following the enriched gas components are released by thermal desorption.

4. Apparatus for determining a gaseous compound, comprising a sensor array (1) with several gas sensors (2) and a transfer and control unit (16) for the controlled transport of a sample gas stream through the sensor array (1) as well as a bypass connected evaluation computer (20) for capturing all signals of the sensor array (1) and for converting the signals into a characterizing image of the sample gas stream and for storing this characterizing image, characterized in that a switchable three way valve (6) is disposed in a feed line (3) with an inlet port (4) of the sensor array (1), wherein the switchable three way valve (6) is in connection with a selective collection unit (7) and wherein a sideline (12) with a thinning unit (13) joins between the three way valve (6) and the sensor array (1).

5. Apparatus according to claim 4, characterized in that the selective collection unit (7) is equipped with an automatically controllable feed transport pump (10) reversible in its transport direction.

6. Apparatus according to claim 5, characterized in that the selective collection unit (7) comprises an adsorber (8) and a heater (9).

7. Apparatus according to claim 4, characterized in that the thinning unit (13) comprises an automatically controllable feed transport pump (14) and an air filter.

8. Method for determining gaseous compounds, wherein a sample gas stream is lead to a sensor array (1) with several gas sensors (2), wherein the electrical output signals of the individual gas sensors (2) are captured by the evaluation computer (20), wherein the electrical output signals are converted into a characterizing image, are stored and are compared with the characterizing images of other gas mixtures, characterized in that the sample gas stream possibly contains easily volatile gas components, wherein the sample gas stream is separated and freed of easily volatile gas components and in the following is thinned with a stream of air prior to the feeding into the sensor array (1) and wherein thereby the concentration of the sample gas stream is kept constant to a predetermined value below the saturation concentration for obtaining a comparable characterizing image.

9. Method according to claim 8, characterized in that the medium and hardly volatile gas components of the sample gas stream are separated from the easily volatile gas components of the sample gas stream by adsorption and in the following the enriched gas components are released by thermal desorption.

10. Apparatus for determining of gaseous compound, comprising a sensor array (1) with the several gas sensors (2) and the transfer and control unit (16) for the controlled transport of a sample gas stream through the sensor array (1) as well as a bypass connected evaluation computer (20) for capturing all signals of the sensor array (1) and for converting the signals into a characterizing image of the sample gas stream and for storing this characterizing image, characterized in that a switchable three-way valve (6) is disposed in a feed line (3) with an inlet port (4) of the sensor array (1), wherein the switchable three-way valve (6) is in connection with a selective collection unit (7) for separating and freeing of easily volatile gas components and wherein a sideline (12) with a thinning unit (13) joins between the three way valve (6) and the sensor array (1) for maintaining the concentration of the sample gas stream constant at a predetermined value below the saturation concentration.

11. Apparatus according to claim 10, characterized in that the selective collection unit (7) is equipped with an automatically controllable feed transport pump (10) reversible in its transport direction.

12. Apparatus according to claim 11, characterized in that the selective collection unit (7) comprises an adsorber (8) and a heater (9) as well as a separate feed transport pump (10) with a flow sensor (11) for the feed transport pump (10).

13. Apparatus according to claim 11, characterized in that the thinning unit (13) comprises an automatically controllable feed transport pump (14), a flow sensor (15) for the feed transport pump (14), and the air filter.

14. A method for determining gaseous compounds comprising the steps:
separating and freeing a sample gas stream of easily volatile gas components;
thinning the sample gas stream with a stream of air prior to a feeding into a sensor array (1);
leading the sample gas stream to the sensor array (1) with several gas sensors (2);
capturing individually electrical output signals of the gas sensors (2) with an evaluation computer (20);
converting the electrical output signals into a characterizing diagram; storing the characterizing diagram;
comparing the characterizing diagram with diagrams of other gas mixtures;
keeping thereby the concentration of the sample gas stream constant to a predetermined value below a saturation concentration for obtaining a comparable characterizing diagram.

15. The method according to claim 14, further comprising separating medium volatile gas components and hardly volatile gas components of the sample gas stream from the easily volatile gas components of the sample gas stream by adsorption; and releasing the enriched gas components by thermal desorption thereafter.

16. The method according to claim 14 further comprising the step:
fixing a work point of the gas sensor (2) in a lower region of a nonlinear concentration curve of the gas sensor (2) for obtaining a most sensitive response of the gas sensor (2) and a quickest response of the gas sensor(2).

17. The method according to claim 14 further comprising the step:
thinning the sample gas stream with fresh air for linearizing the characterizing curves of the individual gas sensors.

18. The method according to claim 14 further comprising the step:
comparing measurements with characterizing images of a gas mixture with high precision and independent of concentration with the evaluation computer (20).

19. The method according to claim 14 further comprising the step:
continuously monitoring the mixing process by the evaluation computer (20);
continuously regulating the mixing process by the evaluation computer (20);
optically imaging the characterizing diagram of a gas compound by the evaluation computer (20).

20. An apparatus for determining of a gaseous compound, comprising
several gas sensors (2) forming a sensor array (1);
a feed line (3) with an inlet port (4) connected to the sensor array (1);
a transfer and control unit (16) for a controlled transport of a sample gas stream through the sensor array (1);
an evaluation computer (20) connected as a bypass for capturing all signals of the sensor array (1) and for converting the signals into a characterizing diagram of the sample gas stream and for storing this diagram;
a switchable three-way valve (6) disposed in the feed line (3) of the sensor array (1);
a selective collection unit, wherein the switchable three-way valve (6) is in connection with the selective collection unit (7) for separating and freeing of easily volatile gas components;
a thinning unit (13);
a sideline (12) with the thinning unit (13) joining between the switchable three-way valve (6) and the sensor array (1) for maintaining the concentration of the sample gas stream constant at a predetermined value below the saturation concentration.

21. The apparatus according to claim 20 further comprising
an automatically controllable feed transport pump (10) reversible in its transport direction furnished to the selective collection unit (7).

22. The apparatus according to claim 20 further comprising
an adsorber (8) furnished at the selective collection unit (7);
a heater (9) furnished at the selective collection unit (7);
a separate feed transport pump (10) furnished at the selective collection unit (7); a flow sensor (11) furnished to the feed transport pump (10).

23. The apparatus according to claim 20 further comprising an automatically controllable feed transport pump (14) furnished to the thinning unit (13);
a flow sensor (15) furnished to the thinning unit (13) for connection to the feed transport pump (14);
an air filter furnished to the thinning unit (13).

24. The apparatus according to claim 20, wherein the sensor array (1) includes a semiconductor gas sensor.

25. The apparatus according to claim 20, wherein the evaluation computer (20) controls a switchable three way valve (6) for controlling the sample gas stream, which sample gas stream is lead over the selective collection unit or passed by the selective collection unit as desired.

26. The apparatus according to claim 20 further comprising an outlet port (5) connected to the transfer and control unit (16).

27. The apparatus according to claim 20, wherein the evaluation computer (20) is connected to flow sensors (11, 15, 18) through connection lines.

28. The apparatus according to claim 20 further comprising a feed transport pump (17) of the transport and control unit (16), wherein the feed transport pump (17) sucks in a predetermined flow of the gas mixture through the inlet port (4) and transports the predetermined flow of the gas mixture through the sensor array 1.

29. The apparatus according to claim 20, wherein a mixing ratio of the sample gas stream is calculated by the evaluation computer (20) and furnished as a display signal the evaluation computer (20).

30. The apparatus according to claim 20, wherein the evaluation computer (20) serves for continuously monitoring and regulating a mixing process.

31. The apparatus according to claim 20, wherein the evaluation computer (20) optically images a characterizing diagram of a gas compound.

32. The apparatus according to claim 20, wherein the evaluation computer (20) optically images and stores a sample pattern of a gas mixture.

33. The apparatus according to claim 20 further comprising a reversible feed transport pump (10) for filling the selective collection unit (7) by the suction power of the reversible feed transport pump (10) and for emptying again the selective collection unit (7) based on the pressure power of the reversible feed transport pump (10).

* * * * *